United States Patent [19]
Palmer et al.

[11] Patent Number: 5,977,302
[45] Date of Patent: Nov. 2, 1999

[54] LIQUID PHASE PROCESS FOR THE PREPARATION OF GNRH PEPTIDES

[75] Inventors: David C. Palmer, Doylestown; Ahmed Abdel-Magid, Lansdale; Michael S. Breslav, Amber, all of Pa.; Urs P. Eggmann, Flurligen, Switzerland; Bruce Harris, Abington, Pa.; Mark L. Haslego, Chalfont, Pa.; Kirk L. Sorgi, Doylestown, Pa.

[73] Assignee: Ortho-McNeil Pharmaceutical, Inc., Raritan, N.J.

[21] Appl. No.: 09/195,049

[22] Filed: Nov. 18, 1998

Related U.S. Application Data

[60] Provisional application No. 60/065,969, Nov. 20, 1997.

[51] Int. Cl.$^6$ .................................... C07K 7/06
[52] U.S. Cl. ..................... 530/339; 530/344; 530/345; 530/333; 530/328; 514/15
[58] Field of Search ................... 530/313, 335, 530/337, 338, 339, 344, 345; 514/15

[56] References Cited

U.S. PATENT DOCUMENTS

| | | | |
|---|---|---|---|
| 5,169,932 | 12/1992 | Hoeger et al. | 530/313 |
| 5,296,468 | 3/1994 | Hoeger et al. | 514/15 |
| 5,352,796 | 10/1994 | Hoeger et al. | 548/265.2 |
| 5,506,207 | 4/1996 | Rivier et al. | 514/15 |
| 5,580,957 | 12/1996 | Hoeger et al. | 530/345 |

FOREIGN PATENT DOCUMENTS

| | | |
|---|---|---|
| WO 91/19737 | 6/1991 | European Pat. Off. . |
| WO 94/19370 | 2/1994 | European Pat. Off. . |
| WO 91/06543 | 10/1990 | WIPO . |
| WO 92/17025 | 3/1992 | WIPO . |
| WO/95/25741 | 3/1995 | WIPO . |
| WO 97/34923 | 2/1997 | WIPO . |
| WO 97/34924 | 2/1997 | WIPO . |

OTHER PUBLICATIONS

J. Med. Chem. 1992, 35 pp. 4270–4278 Gonadotropin–Releasing Hormone Antagonists with N–Triazolyornithine,—Lysine, OR–P–Aminophenylalalanine Residues at Positions 5 and 6.

J. Med. Chem. 1991, 34, pp. 2395–2402 Novel Gonadotropin–Releasing Hormone Antagonists: Peptides Incorporating Modified N–Cyanoguanidino Moieties.

Biochemical and Biophysical Research Communications vol. 176, No. 1, 1991, Apr. 15, 1991 pp. 406–412 Gonadotropin Releasing Hormone Antagonists: Novel Structures Incorporating N–Cyano Modified Guanidine Moieties.

J. Med. Chem. 1986, 29, pp. 1846–1851 New Effective Gonadotropin Releasing Hormone Antagonists with Minimal Ppotency for Histamine Release In Vitro.

J. Am. Chem. Soc. 1990, 112, pp. 9624–9626 General Method for Incorporation of Modified N–Cyanoguanidino Moletities on Selected Amino Functions During Solid Phase Peptide Synthesis.

J. Med. Chem. 1995, 38 pp. 2649–2662 Gonadotropin–Releasing Hormone Antagonists: Novel Members of the Azaline B Family.

*Primary Examiner*—F. T. Moezie
*Attorney, Agent, or Firm*—Kenneth J. Dow

[57] ABSTRACT

A liquid phase process for preparing GnRH peptide analogs of the formula:

$$G\text{-}AA_1\text{-}(A)D\text{-}Phe\text{-}AA_3\text{-}AA_4\text{-}(R_2)\text{-}AA_5\text{-}AA_6AA_7\text{-}AA_8\text{-}Pro\text{-}AA_{10}\text{-}NH_2$$

Formula 1
which comprises:

(a) reacting a peptide of the formula:

$$T\text{-}(R_2)AA_5\text{-}AA_6\text{-}X$$

where T is $(P_2)AA4$ or $P_2$ and X is $AA_7$—OH or is —OH, with a peptide of the formula:

$$X'\text{-}AA_8\text{-}Pro\text{-}AA_{10}\text{-}NH_2$$

or acid-addition salt form thereof, where X' is $AA_7$ when X is absent and X' selected from P-Ala, Gly, GABA, the D- and L- isomers of Ala, amino isobutyric acid, 6-amino-hexanoic acid, Ser, Thr, His, Tyr, Asn, and Gln' is absent when X is $AA_7$—OH;

in a liquid reaction medium in the presence of a peptide coupling reagent and a strong organic amine base to obtain a product of the formula:

$$T\text{-}(R_2)AA_5\text{-}AA_6\text{-}AA_7\text{-}AA_8\text{-}Pro\text{-}AA_{10}\text{-}NH_2$$

(b) removing the $P_2$ protecting group at the N-terminus, and

(c) reacting the product of step (b) or an acid addition salt thereof, with a peptide of the formula:

$$G\text{-}AA_1\text{-}(R_1)D\text{-}Phe\text{-}AA_3\text{-}T'$$

or acid-addition salt form thereof, where T' is $AA_4$—OH when T is absent and is absent when T is $P2\text{-}AA_4$, in a liquid reaction medium to obtain a GnRH peptide of the formula:

$$G\text{-}AA_1\text{-}(A)D\text{-}Phe\text{-}AA_3\text{-}AA_4\text{-}(R_2)AA_5\text{-}AA_6\text{-}AA_7\text{-}AA_8\text{-}Pro\text{-}AA_{10}\text{-}NH_2.$$

14 Claims, 4 Drawing Sheets

FIG. 1 Critical Couplings; Preparation of "Protected" Azaline B (1/10:8Z fragment)

FIG. 2 Preparation of the 5/6 Fragment

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1..3
        (D) OTHER INFORMATION: /product= "derivative of alanine"

(ix) FEATURE:
        (A) NAME/KEY: Modified-site
        (B) LOCATION: 5..6
        (D) OTHER INFORMATION: /product= "amino-substituted
            phenylalanine"

(ix) FEATURE:
        (A) NAME/KEY: Modified-site
        (B) LOCATION: 10
        (D) OTHER INFORMATION: /product= "D-isomer of alanine"

(xi) SEQUENCE DESCRIPTION: SEQ ID NO:1:

Xaa Xaa Xaa Ser Xaa Xaa Leu Lys Pro Xaa
    1               5                   10

(2) INFORMATION FOR SEQ ID NO:2:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1..3
        (D) OTHER INFORMATION: /product= "derivative of alanine"

(ix) FEATURE:
        (A) NAME/KEY: Modified-site
        (B) LOCATION: 5..6
        (D) OTHER INFORMATION: /product= "derivative of
            phenylalanine"

(ix) FEATURE:
        (A) NAME/KEY: Modified-site
        (B) LOCATION: 10
        (D) OTHER INFORMATION: /product= "D-isomer of alanine"

(xi) SEQUENCE DESCRIPTION: SEQ ID NO:2:

Xaa Xaa Xaa Ser Xaa Xaa Leu Lys Pro Xaa
    1               5                   10

(2) INFORMATION FOR SEQ ID NO:3:

```
    (i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "see page 5 of the
            specification"

(ix) FEATURE:
        (A) NAME/KEY: Modified-site
        (B) LOCATION: 2
        (D) OTHER INFORMATION: /product= "D-isomer of
            phenylalanine"

(ix) FEATURE:
        (A) NAME/KEY: Modified-site
        (B) LOCATION: 3..8
        (D) OTHER INFORMATION: /product= "see page 5 of the
            specification"

(ix) FEATURE:
        (A) NAME/KEY: Modified-site
        (B) LOCATION: 10
        (D) OTHER INFORMATION: /product= "see page 5 of the
            specification"

(xi) SEQUENCE DESCRIPTION: SEQ ID NO:3:

Xaa Xaa Xaa Xaa Xaa Xaa Xaa Xaa Pro Xaa
   1               5                   10

(2) INFORMATION FOR SEQ ID NO:4:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "D-isomer of
            phenylalanine"

(xi) SEQUENCE DESCRIPTION: SEQ ID NO:4:

Ser Phe Xaa Leu
   1

(2) INFORMATION FOR SEQ ID NO:5:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "derivative of alanine"

(ix) FEATURE:
        (A) NAME/KEY: Modified-site
        (B) LOCATION: 2
        (D) OTHER INFORMATION: /product= "derivative of
            phenylalanine"
```

```
        (ix) FEATURE:
             (A) NAME/KEY: Modified-site
             (B) LOCATION: 3
             (D) OTHER INFORMATION: /product= "derivative of alanine"

(xi) SEQUENCE DESCRIPTION: SEQ ID NO:5:

Xaa Xaa Xaa Ser
         1

(2) INFORMATION FOR SEQ ID NO:6:

(i) SEQUENCE CHARACTERISTICS:
             (A) LENGTH: 10 amino acids
             (B) TYPE: amino acid
             (C) STRANDEDNESS:
             (D) TOPOLOGY: linear (ii) MOLECULE TYPE: peptide (ix) FEATURE:
             (A) NAME/KEY: Modified-site
             (B) LOCATION: 2
             (D) OTHER INFORMATION: /product= "derivative of
                 phenylalanine"

(ix) FEATURE:
             (A) NAME/KEY: Modified-site
             (B) LOCATION: 3
             (D) OTHER INFORMATION: /product= "derivative of alanine"

(ix) FEATURE:
             (A) NAME/KEY: Modified-site
             (B) LOCATION: 5..6
             (D) OTHER INFORMATION: /product= "derivative of
                 phenylalanine"

(ix) FEATURE:
             (A) NAME/KEY: Modified-site
             (B) LOCATION: 10
             (D) OTHER INFORMATION: /product= "D-isomer of alanine"

(xi) SEQUENCE DESCRIPTION: SEQ ID NO:6:

Xaa Xaa Xaa Ser Xaa Xaa Leu Lys Pro Xaa
         1               5               10
```

LIQUID PHASE PROCESS FOR THE PREPARATION OF GNRH PEPTIDES

This Appln. claims benefit of Provisional Appln. No. 60/065,969 Nov. 20, 1997.

FIELD OF THE INVENTION

The present invention relates generally to liquid phase processes for the preparation of biologically active peptides. More particularly, it relates to the liquid phase synthesis of peptides having activity as GNRH antagonists which inhibit gonadal function and the release of the steroidal hormones progesterone and testosterone.

BACKGROUND OF THE INVENTION

GnRH is a hypothalmic hormone which triggers the release of the gonadotropic hormones, particularly leutinizing hormone. These hormones regulate the functioning of the gonads to produce testosterone in the testes and estrogen in the ovaries; and they also regulate the production and maturation of gametes. Mammalian GnRH is a well known decapeptide as described in U.S. Pat. No. 4,072,668.

GnRH peptide analogs which are antagonistic to endogeneous GnRH and inhibit the secretion of gonadotropins and the release of steroids by the gonads are known from U.S. Pat. Nos. 5,506,207 and 5,169,932. These compounds are analogs of the decapeptide GnRH which include modified amino acids in the 5 and 6 position. Particularly useful are the peptide analogs which have the general formula:

Ac-β-D-2NAL-(4CI)D-Phe-D-3PAL-Ser-AA$_5$-D-AA$_6$-Leu-Lys(isopropyl)-Pro-D-Ala-NH$_2$(SEQ ID No:1)

wherein AA$_5$ and AA$_6$ are residues of amino- substituted phenylalanine (or its equivalent) where the substituent is preferably in the 4-position and is preferably an acylating agent of 5 carbon atoms or less or one which contains an unsaturated heterocyclic ring containing from 2 to 4 nitrogen atoms. Particularly useful is the GnRH peptide analog known as Azaline B, which contains an "Aph(Atz)" substituent, that is, a 5 membered triazole ring (specifically, a 1,2,4-triazole) as the substituent in the 4 position of the amino substituted phenylalanine of both AA$_5$ and AA$_6$. Also useful are the peptides known as Azaline C, which has a methyl group on the backbone nitrogen of residue 5, and Acyline, which has an acetamido group as the substituent in the 4 position of the substituted phenylalanine. Further useful GnRH peptide analogues are reported by Rivier et al, J. Med. Chem, 1995, 38, 2649–2662, wherein the amino substituent is acylated with a simple amino acid residue, e.g. Gly, Ser, Ala, etc, followed by deprotection and triazole construction.

Previously, as described in the patents mentioned above, these GnRH analogs have generally been prepared by a classical solid phase peptide synthesis (SPPS) in which the peptide chain is elongated via sequential addition of amino acids to the resin-bound C-terminal amino acid by reaction with an excess of an appropriately activated and protected amino acid. In this method, to maximize coupling efficiencies and reduce side reactions, all couplings are performed with a minimal 3–5 fold excess of activated amino acid, coupling reagents and additives and all reactive side chain functionalities must be protected throughout the entire synthesis. In Azaline B, the key amino-triazoles on the phenylalanine residues of AA$_5$ and AA$_6$ are generally constructed only after the entire backbone has been assembled and immediately prior to global deprotection with concomitant resin cleavage. In one exception to this Rivier et al, J. Med. Chem, 1995, 38, 2649–2662, reports the construction of the amino-triazole units simultaneously on the protected resin anchored [5–10] hexapeptide followed by incorporation of the remaining 4 amino acids in the usual solid-phase synthesis manner.

While this SPPS procedure provides the GnRH peptides in acceptable yield and purity, the SPPS procedure exhibits several inherent limitations which make it undesirable for large scale production of the peptides. These include:

capacity of the resin which limits the amount of the final product;

expense attributable to the C-terminal amide cleavable resins and the large excesses of coupling reagents, additives, and amino acids required;

necessity of full protection for all reactive side chains as in the hydroxy group in Ser$^4$, the aromatic amino groups in Aph$^5$, D-Aph$^6$ and the ε-i-propylamino group in Lys(i-Pr)$^8$;

strongly acidic conditions required to affect global deprotection and cleavage of the peptide from the resin.

In addition, because each amino acid is incorporated in a separate reaction, any side reaction or decoupling of the peptide in the later stages requires the process to be repeated from the beginning. Accordingly, there is a need for an improved process for the preparation of GnRH peptide analogs which is amenable to large scale manufacture. Other methods for the bulk scale production of peptides include liquid phase peptide synthesis (LPPS), enzymatic synthesis, or fermentation with genetically manipulated microorganisms. However, none of these methods have been applied to the production of GnRH peptide analogs.

SUMMARY OF THE INVENTION

To address the limitations associated with the solid phase syntheses of GnRH peptide analogs, a liquid (or solution) phase peptide syntheses (LPPS) method is provided in which the GnRH peptide is assembled via condensation of judiciously selected peptide fragments using critical fragment couplings. In this method, the critical fragment couplings are kept to a minimum number to reduce potential side reactions and epimerization of the activated C-terminus. Accordingly, the peptide is synthesized by an LPPS method by first preparing the critical central peptide fragments of AA$_5$ and AA$_6$ with the side chains fully elaborated and then assembling the peptide through a "4–2–4", "3–3–4" or "3–4–3" fragment assembly pattern. In the preferred "4–2–4" assembly pattern embodiment, the Aph(Atz) residues are constructed and incorporated simultaneously. Alternative coupling patterns in accordance with the LPPS method of the present invention, such as a "2–2–2–2–2" pattern, are also contemplated to be within the scope of this invention.

More particularly, in accordance with the invention, a process for preparing GnRH peptide analogs of the formula:

G-AA$_1$-(A)D-Phe-AA$_3$-AA$_4$-(R$_2$)AA$_5$-AA$_6$-AA$_7$-AA$_8$-Pro-AA$_{10}$-NH$_2$ (SEQ. ID NO. 3)

Formula 1 or an acid addition salt thereof, wherein G is an acyl group having 7 or less carbon atoms; AA$_1$ is (A)D-Phe, (B)D-Trp, or β-D-NAL; A is H, Cl, F, NO$_2$, Br, CH$_3$, or OCH$_3$; B is H, NO2, NH2, OCH$_3$, F, Cl, Br or CH$_3$; AA$_3$ is D-PAL, β-D-NAL or (B)D-Trp; AA$_4$ is Ser or P$_1$-Ser wherein Pis a hydroxy protecting group; R$_2$ is H, N$^\alpha$CH$_3$ or N$^\alpha$CH$_2$CH$_3$; AA$_5$ is Aph(P$_2$), Aph(Ac),Aph(atz), Lys(P$_2$), Lys(atz), Aph (Q-Atz) or Lys(Q-Atz); $AA_6$ is D-Aph($P_2$), D-Aph(ac), D-Aph(atz), D-Lys($P_2$), D-Lys(atz), D-Aph(Q-Atz) or D-Lys(Q-Atz); wherein $P_2$ is an amino protecting group; Ac is acetyl, atz is 5'-(3'-amino-1H-1',2',4'-triazolyl), and Q is the acyl residue of an amino acid; $AA_7$ is Leu, NML, Nie or Phe; $AA_8$ is iPr-Lys, ($P_2$)iPr-Lys, or Arg; $AA_{10}$ is D-Ala, Gly, $NH_2NHCO$ or $NH(R_3)$ wherein $R_3$ is lower alkyl; is provided, which comprises:

(a) reacting a peptide of the formula:

where T is ($P_2$) $AA_4$ or $P_2$ and X is $AA_7$—OH or is —OH, with a peptide of the formula:

or acid-addition salt form thereof, where X' is $AA_7$ when X is absent and X' is absent when X is $AA_7$—OH;

in a liquid reaction medium in the presence of a peptide coupling reagent and a stron organic amine base to obtain a product of the formula:

(b) removing the $P_2$ protecting group at the N-terminus, and (c) reacting the product of step (b) or an acid addition salt thereof, with a peptide of the formula:

or acid-addition salt form thereof, where T' is $AA_4$—OH when T is absent and is absent when T is P2-$AA_4$, in a liquid reaction medium to obtain a GnRH peptide of the formula:

(SEQ. ID NO. 3)

In this synthetic approach the requisite central amino acid fragment containing the fully elaborated amino triazole side chains is prepared first and then assembled with the previously prepared remaining peptide fragments to provide the final product using a minimum number of steps. This approach minimizes the number of reactions involving large peptide fragments. The prior art solid phase synthetic process generally requires sequentially preparing a fully protected peptide backbone followed by introduction of the side chains such as the aminotriazole moiety on $AA_5$ and $AA_6$. In contrast, the process of the present invention allows the side chains to be fully elaborated prior to coupling thereby reducing the use of protecting groups in the synthesis. The requisite fragments are prepared in high yield and purity via the liquid phase technique using stoichiometric amounts of the appropriately protected amino acids, coupling reagents and additives.

The advantages of the LPPS process in contrast to the SPPS process for synthesizing GnRH peptide analogs are:

production of final product is limited only by vessel capacity thus permitting large scale bulk production;

considerable savings can be realized by using stoichiometric or minimal excesses of required amino acids, coupling reagents, additives and reactants;

provides carefully controlled coupling chemistry which reduces unwanted side reactions or eliminates the necessity for any side chain protection;

the final product is isolated directly by precipitation eliminating the necessity for lyophilization.

In another aspect of the invention, a process for preparing the dipeptide $AA_5$–$AA_6$ fragment of the formula:

wherein $R_1$ is $P_2$- Ser, $P_2$-Ser($P_1$)- or $P_2$ where $P_1$ is a hydroxy protecting group and $P_2$ is an amino protecting group and $R_2$ is Leu, LeuOR where R is alkyl, OH or alkyl, is provided, which comprises:

a) reacting a compound of the formula $P_2$-p-NO2-PheOH with p-$NO_2$-PheOR where R is alkoxy, or an acid addition salt thereof, in the presence of a suitable peptide coupling reagent in a suitable solvent to obtain a dipeptide of the formula:

b) reducing the dipeptide to obtain a compound of the formula:

c) reacting the product of step b) first with diphenyl cyanocarbonimidate or an equivalent reagent and then with hydrazine in a suitable solvent to yield a compound of the formula:

DETAILED DESCRIPTION OF THE INVENTION

Within the group of GnRH analogs defined by Formula 1, the invention is particularly useful for the preparation of certain subgroups. Broadly preferred are the peptides wherein G is an acyl group having 7 or less carbon atoms; $AA_1$ is β-D-NAL; A is 4Cl; $AA_3$ is D-PAL; $AA_4$ is Ser, $R_2$ is H, $NaCH_3$ or $NaCH_2CH_3$; $AA_5$ is Aph(Ac),Aph(atz), Lys(atz), Aph(Q-Atz) or Lys(Q-Atz); $AA_6$ is D-Aph(ac), D-Aph(atz), D-Lys(atz), D-Aph(Q-Atz) or D-Lys(Q-Atz); wherein ac is acetyl, atz is 5'-(3'-amino-1H-1',2',4'-triazolyl), and Q is the acyl residue of an amino acid selected from β-Ala, Gly, GABA, the D- and L- isomers of Ala, amino isobutyric acid, 6-amino-hexanoic acid, Ser, Thr, His, Tyr, Asn and Gln; $AA_7$ is Leu; $AA_8$ is ipr-Lys; and $AA_{10}$ is D-Ala.

The process is particularly useful for the preparation of the GnRH peptide known as Azaline B or its acid addition salt, having the formula:

Ac-β-D-2NAL-(4Cl)D-Phe-D-3PAL-Ser-Aph(Atz)-D-Aph(Atz)-Leu-Lys(isopropyl)-Pro-D-Ala-NH$_2$(SEQ ID No:2)

The term "acyl residue of an amino acid" as used herein means the acyl residue of a naturally occurring amino acid, a racemic amino acid, or synthetic amino acid. Suitable amino acids are as described hereinabove.

The terms "hydroxy protecting group" for $P_1$ and "amino protecting group" for $P_2$ as used herein mean any of the known protecting groups used in the art of organic synthesis, for example as described in Principles of Peptide Synthesis, $2^{nd}$ Ed., M. Bodanszky, Springer-Verlag, Berlin, 1993; The Peptides, Vol 3 Protection of Functional Groups in Peptide Synthesis, eds E. Gross and J. Meienhofer, Academic Press, New York, 1981; and Protective Groups in Organic Synthesis, $2^{nd}$ Ed., T. W. Greene and P. G. M. Wuts, John Wiley & Sons, New York, 1991, hereby incorporated by reference.

Examples of hydroxy-protecting groups P, which are known to those skilled in the art, include, for example benzyl, tetrahydropyranyl, tri($C_1$–$C_6$)alkylsilyl, t-butyl, 2-methoxyethoxymethyl (MEM), 4-dimethylcarbamoylbenzyl and O-phenoxyacetyl ethers. The hydroxy-protecting group selected is preferably one that is easily removable in the reaction process.

Examples of suitable amino protecting groups include but are not limited to acetyl (Ac), benzoyl (Bz), trifluoroacetyl (Tfa), toluenesulfonyl (Tos), benzyl (Bn), triphenylmethyl (Trt), o-nitrophenyl-sulfenyl (Nps), benzyloxycarbonyl (Cbz or Z), t-butoxycarbonyl (Boc), allyloxycarbonyl (alloc), 9-fluorenylmethyloxycarbonyl (Fmoc), 2-bromo-benzyloxycarbonyl (2-Br-Z), 2-chloro-benzyloxycarbonyl (2-Cl-Z), t-butyl-dimethylsilyloxycarbonyl, [2-(3,5-dimethoxyphenyl)-propyl-2-oxycarbonyl](Ddz), 2,2,2-trichloroethyloxycarbonyl (Troc), biphenylylisopropyloxycarbonyl (Bpoc), and o-nitrobenzyloxycarbonyl.

As used herein, the abbreviations for the individual amino acid residues above are in accordance with the conventional definitions for amino acids and as set forth in U.S. Pat. No. 5,296,468, hereby incorporated by reference. Accordingly, β-D-NAL means the D-isomer of alanine which is substituted by naphthyl on the β-carbon atom; β-D-PAL means alanine which is substitued by 3-pyridyl on the carbon atom. By Aph is meant 4NH$_2$Phe; atz means 5'-(3'-amino-1H-1', 2',4'-triazolyl). NML means $N^\alpha CH_3$-L-Leu, i-Lys means isopropyl lysine, D-p-Cal means (4Cl)D-Phenylalanine. Other abbreviations and symbols use herein are as follows: HOAc is acetic acid, DMF is N,N-dimethylformamide, MeOH is methanol, THF is tetrahydrofuran, EtOAc is ethyl acetate, EtOH is ethanol, IPA is isopropanol, NMP is 1-methyl-2-pyrrolidone, TFE is 2,2,2-trifluoroethanol, DMA is dimethylacetamide, DMSO is dimethyl sulfoxide, DCM is dichloromethane, MTBE is methyl t-butyl ether, MeCN is acetonitrile, HOBt is 1-hydroxybenzotriazole, HOAt is 1-hydroxy-7-aza-benzotriazole, HOSu is N-hydroxysuccinimide, HOOBT or ODBHT is 3,4-dihydro-3-hydroxy4-oxo-1,2,3-benzotriazine, DCC is 1,3 dicyclohexylcarbodiimide, DIC is 1,3-diisopropyl-carbodiimide, EDAC or WSCDI is 1-(dimethylaminopropyl)-3-ethylcarbodiimide hydrochloride, TFA is triflouroacetic acid,. IBCF is i-butylchloroformate, IPCF is isopropylchloroformate, NMM is N-methylmorpholine, DIPEA is N,N'-diisopropyl ethyl amine, TEA is triethyl amine, DPCCI is diphenylcyanocarbonimidate, Ac$_2$O is acetic anhydride, n-Bu$_4$NOH is tetrabutyl ammonium hydroxide, EEDQ is N-ethoxycarbonyl-2-ethoxy-1,2-dihydroquinoline, TNTU is 2-(5-norbornen-2,3-dicarboximido)-1,1,3,3-tetramethyluronium tetrafluoroborate, TSTU is 2-succinimido-1,1,3,3-tetramethyluronium tetrafluoroborate, HATU is O-(7-azabenzotriazol-1-yl)-1,1,3,3-tetramethyluronium hexafluorophosphate, HBTU is O-(benzotriazol-1-yl)-1,1,3,3-tetramethyluronium hexafluorophosphate, TBTU is O-(benzotriazol-1-yl)-1,1,3, 3-tetramethyluronium tetrafluoroborate, BOP is benzotriazole-1-yl-oxy-tris(dimethylamino)phosphonium hexafluorophosphate, BOP-Cl is N,N-bis-(2-oxo-3-oxazolidinyl)phosphonic dichloride, PyBOP is benzotriazole-1-yl-oxy-tris-pyrrolidinophosphonium hexafluorophosphate, PyBroP is bromo-tris-pyrrolidino-phosphonium hexafluorophosphate, T3P is propane phosphonic acid anhydride, TCFH is tetramethylchloroformamidinium hexafluorophosphate, and TFFH is tetramethylfluoroformamidinium hexafluorophosphate.

Figure 1:
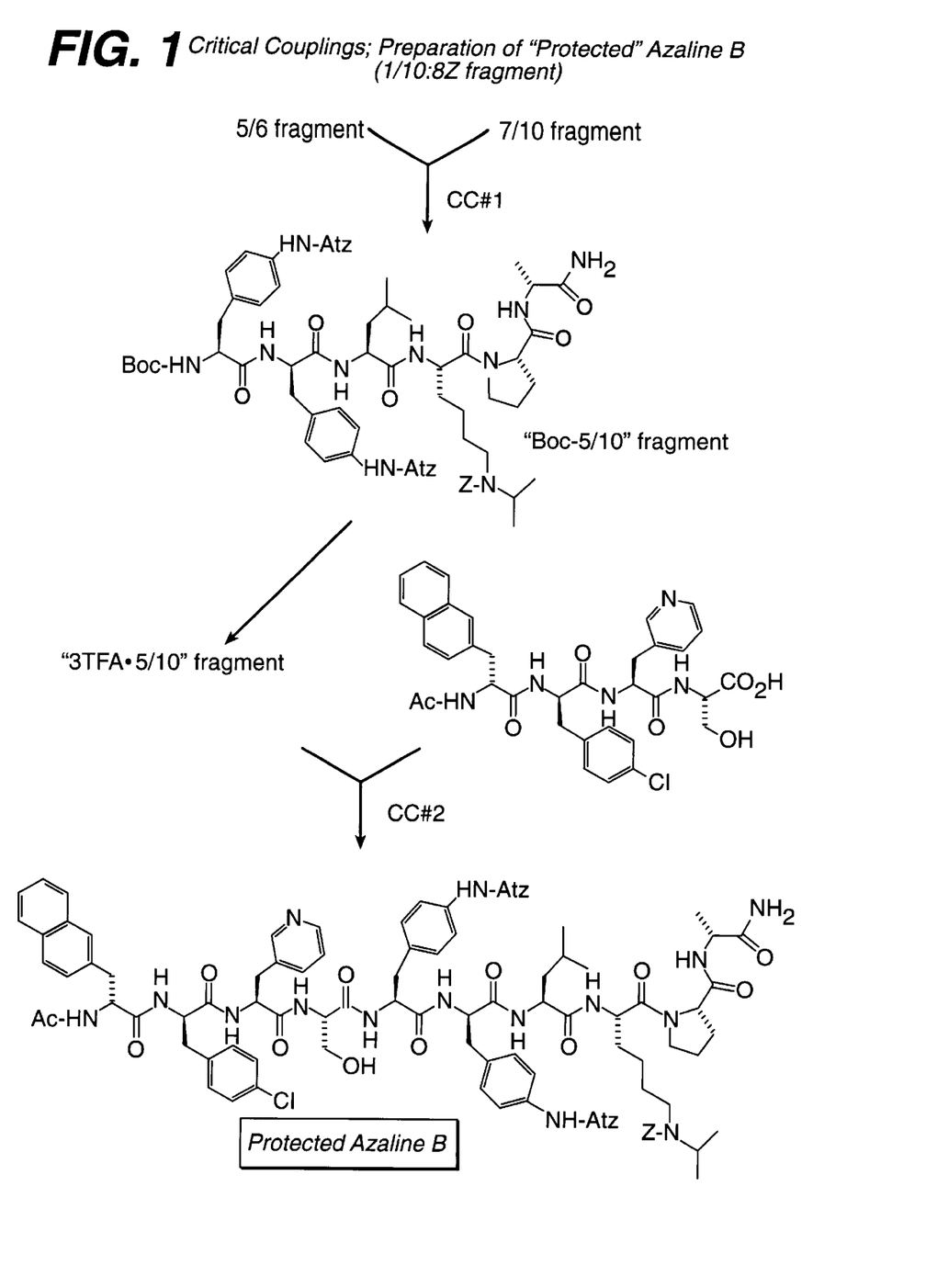
FIG. 1 is a scheme for synthesizing Azaline B (SEQ. ID NO:2) following the method of the present invention.

The liquid phase process of the present invention is schematically illustrated in FIG. 1. with reference to the preferred method for the preparation of the Azaline B peptide. In accordance with the method shown in FIG. 1, the decapeptide is prepared by assembling the peptide from three previously prepared peptide fragments. The three peptide fragments are the central "5/6" dipeptide fragment of $AA_5$ and $AA_6$; the "7/10" fragment of $AA_7$ through $AA_{10}$; and the "1/4" fragment of $AA_1$ through $AA_4$.

FIG. 1 illustrates the critical coupling reactions for assembling the decapeptide. In the first coupling, the Boc 5/6 fragment, Boc-Aph(Atz)-D-Aph(Atz) is reacted with the 7/10 fragment Leu-Lys(ε-Z, ε-isopropyl)-Pro-D-Ala-NH$_2$ which has previously been converted to the corresponding TFA salt by reaction with neat TFA. Other acid addition salts such as the HCL salt may also be employed as well as the free base. This 7/10:8Z fragment is coupled with the Boc 5/6 OH fragment in the presence of a peptide coupling agent and an inert solvent at about −10° C. to room temperature to give the Boc 5/10:8-Z fragment, Boc-Aph(Atz)-D-Aph(Atz)-Leu-Lys(ε-Z, ε-isopropyl)-Pro-D-Ala-NH$_2$. Preferably, the ε-amino group group on $AA_8$ is protected with a suitable amino protecting group such as carbobenzyloxy (Z as shown in FIG. 1). Examples of suitable peptide coupling agents include but are not limited to: DCC, DIC, TBTU, WSCDI, EEDQ, HBTU, TNTU, TSTU, HATU, BOP, BOP-Cl, PyBOP, PyBroP, IPCF, IBCF and propane phosphonic acid anhydride. Examples of common peptide coupling additives are HOBt, HOOBt, HOSu and HOAt while examples of common bases are TEA, NMM, DIPEA, and 2,4,6-trimethylpyridine (sym-collidine). The preferred agents for this particular fragment coupling are HOBT, DIPEA and TBTU. Unexpectedly, it has been found that the use of multiple equivalents of DIPEA or similar strong organic amine bases results in only trace amounts of undesired by-products derived from coupling through the atz residue in $AA_5$ and $AA_6$. Solvents for the coupling are chosen for their compatibility with the chosen coupling agent. Suitable solvents include EtOAc, DCM, DMF, DMA, THF, NMP, DMSO, TFE, MTBE and MeCN, where DMF is preferred. The product is recovered by precipitation in an aqueous media of weakly acidic to weakly basic pH. (pH about 4–11). For example, the product is precipitated in an acidic solution containing ammonium acetate or it can also be precipitated directly into a basic solution containing $K_2CO_3$, $Na_2CO_3$, $NaHCO_3$, etc. The Boc protecting group is cleaved by treating with an acid at about −20 to 0° C. under an inert atmosphere. Although a solvent may be used with an acid, such as HCl, the preferred method uses neat trifluoroacetic acid at about 0° C.

In the next step Aph(Atz)-D-Aph(Atz)-Leu-Lys(ε-Z, ε-isopropyl)-Pro-D-Ala-NH$_2$×3 TFA (a.a. 5–10 of SEQ. ID. NO.2) is treated with a peptide coupling agent, an organic base and Ac-β-D-2NAL-(4Cl)D-Phe-D-3PAL-Ser (a.a. 1–4 of SEQ. ID. NO.2) in an inert solvent at about −4 to 10° C. to give Ac-o-D-2NAL-(4Cl)D-Phe-D-3PAL-Ser-Aph(Atz)-D-Aph(Atz)-Leu-Lys(e-Z, e-isopropyl)-Pro-D-Ala-NH$_2$. (SEQ. ID. NO.2) While any of the peptide coupling reagents previously recited may be employed, the preferred peptide coupling agents are HOOBT and TBTU, the preferred solvent is DMF and the preferred organic base is DIPEA.

In the final step, the protecting group on $AA_8$ lysine is cleaved by treatment with a salt in the presence of an acid and a cation scavenger at about −20 to 0° C. under an inert atmosphere. The preferred acid was TFA, the preferred salt was KCl and the preferred scavenger was anisole. After chromatographic purification and removal of the TFA, the free base product, or the acid addition salt thereof, such as the acetate, is then isolated by precipitation. Subsequently, the free base product can be converted to the acid addition salt, such as the acetate, by treatment with an appropriate acid.

In a preferred embodiment, after cleavage of the protecting group on $AA_8$ lysine, an improved procedure for the isolation of the final Azaline B acetate compound is utilized which involves concentration of the purified product in an organic solvent/water mixture prior to evaporation. The product obtained from initial chromatographic purification can be concentrated on a chromatographic column, eluted with an organic solvent such as acetonitrile, treated with an ion-exchange resin to change trifluoroacetate to acetate and precipitated from the acetic acid solution after evaporation and redissolving in acetic acid. Alternatively, the product can be treated with an ion-exchange resin to change trifluoroacetate to an acetate, concentrated by reverse osmosis using osmotic membrane filtration and precipitated from the acetic acid solution after evaporation and redissolving in acetic acid. In either event, concentration of the solution in an organic solvent or organic solvent/water mixture in accordance with this embodiment provides an improved procedure for evaporation and isolation of the acetate product since smaller volumes and milder conditions can be used for removal of the solvent and evaporation to dryness before the precipitation from the acetic acid solution. The improved isolation procedure provides greater yields and higher purity since less product is lost in the isolation process due to the decreased volumes and milder conditions (temperature of evaporation) which may be employed.

Figure 2:
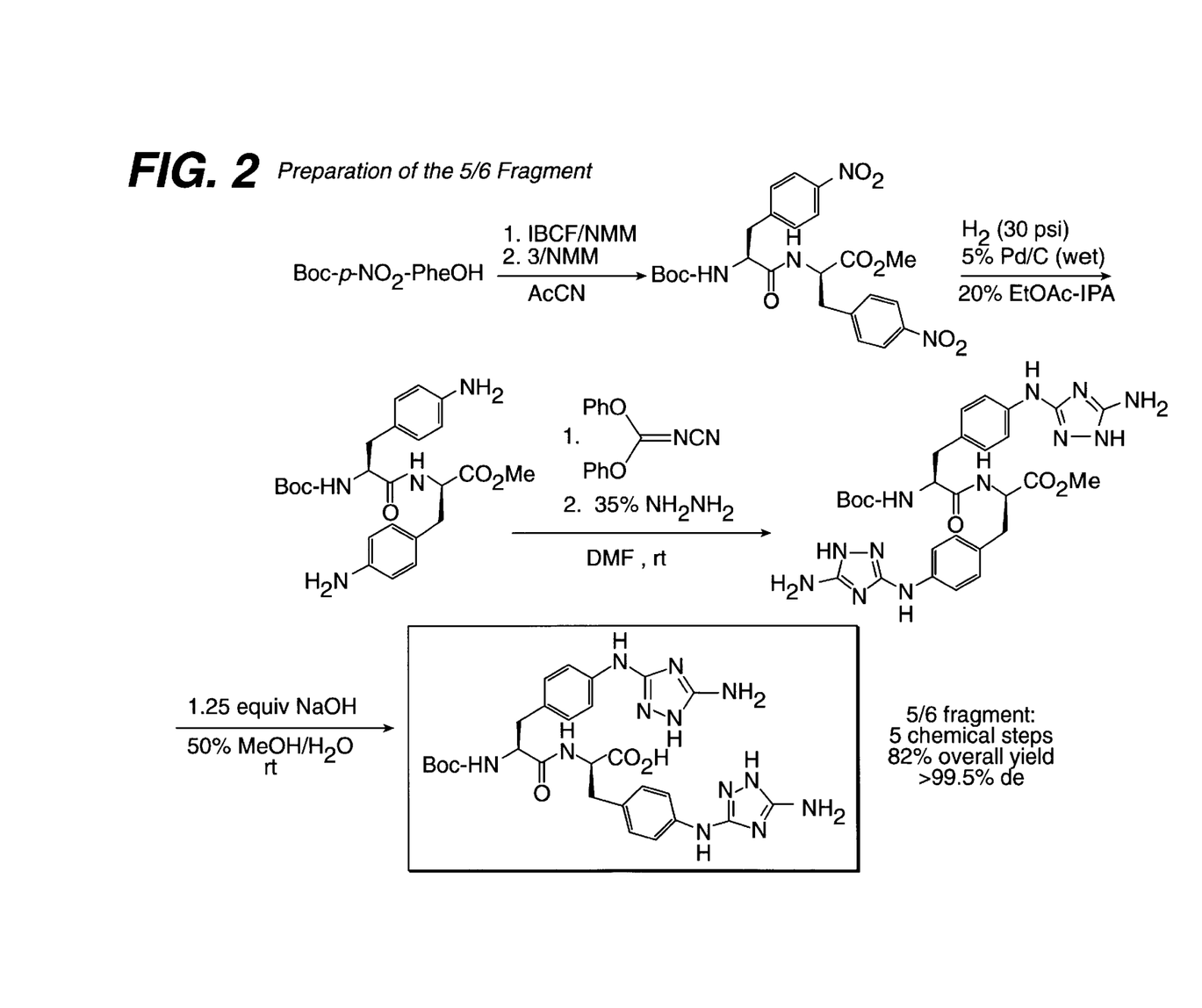
FIG. 2 is a scheme for synthesizing the dipeptide fragment of $AA_5$ and $AA_6$ in Azaline B following the method of the present invention.

FIG. 2 illustrates the synthesis of the central "5/6" dipeptide fragment. In this process, both aminotriazole groups are incorporated simultaneously to generate the fully elaborated fragment, with or without protecting groups, in high yield and purity. Following the reaction as outlined in FIG. 2, Boc-protected p-nitro phenylalanine is reacted with p-nitro-D-phenylalanine methyl ester hydrochloride in the presence of a suitable peptide coupling reagent such as IBCF/NMM in a suitable solvent to obtain the Boc-protected nitro-substituted Phe-Phe dipeptide. A wide variety of coupling agents as previously described, e.g. DCC/HOBt and EDAC/HOBt may also be employed. The nitro groups on the dipeptide are then reduced with a suitable reducing agent to obtain the amino substituted dipeptide:

A wide variety of reducing agents and catalysts may be employed for example palladium/carbon, sodium dithionite, catalytic transfer hydrogenation and the like. The 1,2,4-triazole groups are then formed simultaneously on the amino- substituted phenylalanine groups by reacting the reduced dipeptide first with diphenyl cyanocarbonimidate and then with hydrazine (anhydrous, hydrazine hydrate, 50% aqueous and 35% aqueous hydrazine all work equally well) in a suitable solvent such as DMF. The final "5/6" dipeptide fragment is then obtained by reaction with a suitable base such as sodium hydroxide in a suitable solvent such as methanol/water.

In an alternative process, the central 5/6 dipeptide fragment can be incorporated into a three or four amino acid fragment containing either or both the neighboring serine and/or leucine. To accomplish this the neighboring amino acid can be incorporated into the phenylalanine starting material to yield Boc Ser-p-NO$_2$-Phe-p-NO$_2$-D-PheOR, Boc-p-NO$_2$-Phe-p-NO$_2$-D-Phe-LeuOR or Boc Ser-p-NO$_2$-Phe-p-NO$_2$-D-Phe-LeuOR (SEQ. ID NO. 6) and the atz side chains are then elaborated in an analgous manner as set forth in FIG. 2.

Figure 3A:
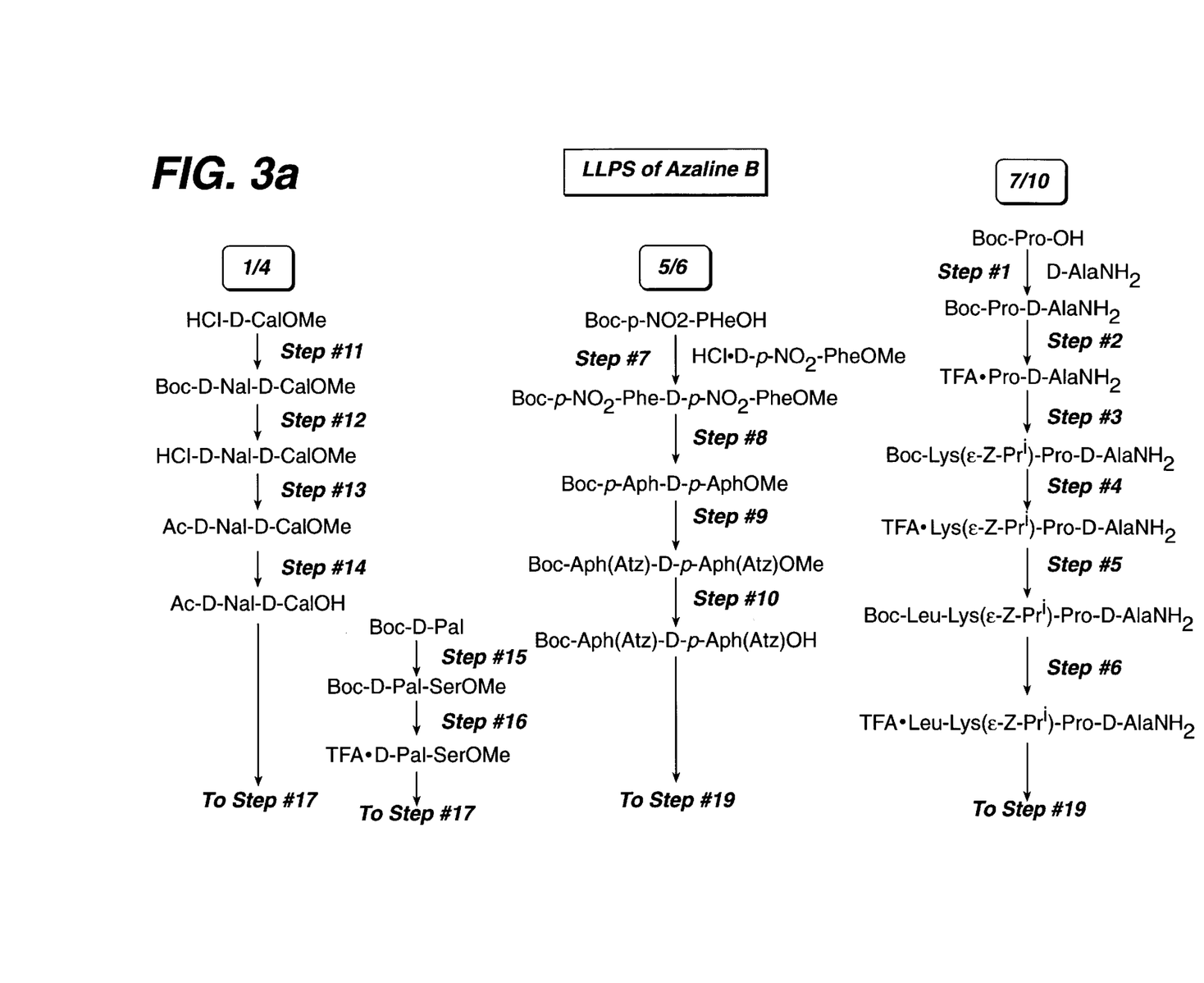
FIG. 3 is an overall scheme for synthesing Azaline B following a specific method of the present invention.
Figure 3B:
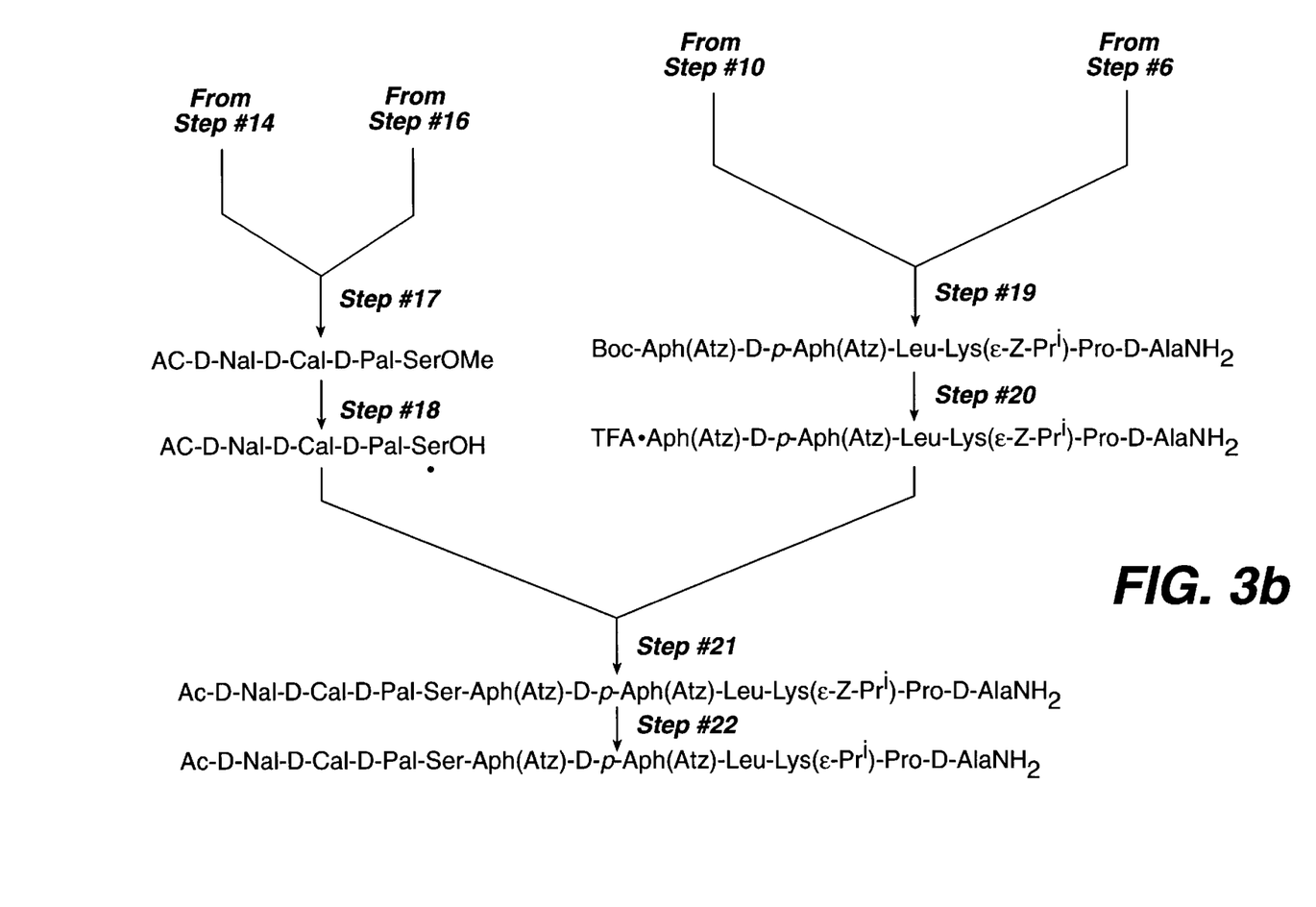

The "7/10" fragment of AA$_7$ through AA$_{10}$; and the "1/4" fragment of AA$_1$ through AA$_4$ used as starting materials for the coupling reactions are likewise prepared by liquid phase chemistry as outlined in FIG. 3. For the 1/4 fragment, the synthesis starts with an ester of H-D-p-Cal such as H-D-p-Cal-OMe*HCl. Other ester groups such as benzyl may also be employed. This compound is then coupled with Boc-protected D-Nal-OH utilizing any of the conventional peptide coupling reagents and solvents as discussed previously. The Boc-protecting group is then cleaved by treatment with an acid. The dipeptide ester is then treated with TEA and acylated by treatment with an appropriate acid anhydride such as acetic anhydride or acid chloride such as acetyl chloride. After removal of the ester by treatment with a base such as aqueous tetrabutylammonium hydroxide, the Ac-D-Nal-D-CalOH dipeptide is coupled with a serine dipeptide ester, D-Pal-SerOCH$_2$Ph as a free base or its acid addition salt using any of the previously discussed techniques for peptide coupling. Other ester groups such as benzyl may be substituted for the methyl ester. Removal of the ester group as mentioned above yields the final 1/4 peptide fragment.

For the 7/10 fragment, the synthesis starts with D-alanine amide as the free base or in the acid addition salt form. This is coupled with Boc-protected proline using the peptide coupling chemistry discussed above, preferably DCCIHOBT/NMM in acetonitrile at 0–5° C. The Boc protecting group is removed with a suitable acid, preferably TFA. Likewise, the remainder of the 7/10 peptide fragment is built up using the coupling chemistry described herinabove.

Alternatively, the requisite fragments used for the coupling reactions can be prepared by solid phase synthesis on a resin in accordance with the prior art. The fragments can then be coupled by liquid phase synthesis in accordance with the invention.

The following examples are meant to illustrate the invention, not to limit it. Other embodiments will be obvious to those skilled in the art and are meant to be within the scope of this invention. The identity of compounds was confirmed by $^1$H NMR, $^{13}$C NMR, MS, combustion analysis, and HPLC comparison with known standards where possible. The chemical purities of all compounds were determined by their HPLC area%. The % epimerization was determined using an HPLC or capillary electrophoresis method capable of affording baseline resolution for the enantiomers or diastereomers in question. In all cases both diastereomers or enantiomers were prepared.

EXAMPLE 1

Synthesis of 7110 fragment of Azaline B

TFA.Leu-Lys($\epsilon$-Z, $\epsilon$-isopropyl)-Pro-D-Ala-NH$_2$ (a.a. 7–10 of SEQ. ID. NO. 2)

Steps 1–2

Preparation of Pro-D-Ala AmidexTFA Using D-Ala Amide HCl

To a clean, dry 2 L glass vessel, charge 0.80 L acetonitrile and begin agitation. Cool the solvent to 0–5° C. and sequentially charge 25.00 g (0.200 mol) D-alanine amide.HCl, 45.40 g (0.220 mol) DCC, 0.27 g (0.002 mol) HOBt, 20.30 g (0.200 mol) N-methylmorpholine and 49.70 9 (0.230 mol) of Boc-proline and allow the reaction mixture to warm to 20–25° C. After 3.5 hours filter the solids from the reaction mixture. Rinse the filtered wet cake with 0.2 L acetonitrile.

The MeCN filtrates are combined and concentrated under vacuum (30° C. @ 15 Torr) to give 99.40 g of an off-white I tan foam. To a 3 L 3 NRB flask charge 0.89 Kg TFA and cool (ice-bath) to 0–5° C. With good agitation charge the crude solid Boc-Proline-D-alanine amide to the cold TFA. After stirring a total of 1 hour the reaction mixture is concentrated to dryness under vacuum (35 ° C. @ 15 Torr). Much of the residual TFA is removed azeotropically with toluene (2×200 mL) after which the product is dried further at 12–15 Torr @ 40° C. for one hour to yield 206.0 g of a crude oil. To this crude product residue is added 0.90 L MTBE at room temperature. The mixture was stirred to induce crystallization/precipitation of the product and the slurry cooled in an ice bath. The solid product is isolated by vacuum filtration and washed with 2×150 mL ice cold MTBE and vacuum dried for 24 hrs. at 40° C. to give 55.0 g of the dipeptide salt as white solid in 91.8% yield from D-alanine amide x HCl. For C$_8$H$_{15}$N$_3$O$_2$×CF$_3$CO$_2$H×0.25 MeCN×0.1H$_2$O (MW=311.31): MS: [M+H]$^+$=186.2 and [2M+H]$^+$=371.3. Anal: Calculated: %C 40.51; %H 5.49; % N 14.62; %F; 18.30; %H$_2$O 0.38. Found: %C 40.71; %H 5.69; % N 14.67; %F 17.34; %H$_2$O 0.43.

Step 3

Preparation of Boc-Lys-N$^\epsilon$(i-Pr, Z)-Pro-D-Ala Amide

In a clean dry 5 L 3 neck round bottom flask (NRBF) dissolve 265.0 g (0.613 mol) of Boc-lysine-N$^\epsilon$(i-Pr, Z) in 1.5 L ethyl acetate. With agitation cool this solution to 0–5° C. in an ice bath and charge 167.0 g (0.558 mol) proline-D-alanine amide TFA salt. To the cool suspension sequentially add 176.0 g (1.740 mol) N-methyl morpholine, 75.4 g (0.558 mol) HOBt and 126.4 g (0.613 mol) DCC. The reaction mixture is warmed to 20–25° C. and stirred for approx. 25 hours whereupon it is cooled to 0–5° C. and 120 mL of water is added. After stirring 10–15 minutes the DCU is removed by filtration and the wet filter cake washed with 2×250 mL EtOAc. The combined EtOAc filtrate was washed successively with 2×0.5 L 10% aq. citric acid and 2×0.5 L saturated aqueous sodium bicarbonate. After drying over MgSO$_4$ filtration and evaporation of the filtrate under vacuum (12–15 torr @ 35° C.) the protected tripeptide is afforded as a very thick oil in a 380 g crude quantitative yield. For C$_{30}$H$_{47}$N$_5$O$_7$×0.33 H$_2$O (MW=595.75): MS: [M+H]$^+$=590. Anal: Calculated: %C 60.49; %H 8.07; %N 11.75; %H$_2$0 1.00. Found: %C 60.53; %H 8.12; %N 10.48; %H$_2$0 1.01.

Step 4

Preparation of TFA-Lys-N$^\epsilon$(i-Pr, Z)-Pro-D-Ala Amide

The flask used in the previous example contains 380.0 g (0.558 mol) Boc-tripeptide. Cool the flask in an ice-bath and charge 3.8 Kg TFA with stirring at 0° C. Stir the reaction mixture at 0° C. for 1.5 hour then concentrate to dryness under vacuum (35–40 ° C. @ 15–20 Torr) Residual TFA is removed azeotropically with 2 X 250 mL toluene and reevaporation to dryness (35–40° C. @ 15–20 Torr). The residual oil is dried further under vacuum (12 Torr) to give 580 g of the tripeptide salt in a crude quantitative yield. For $C_{25}H_{39}N_5O_5 \times 4$ $CF_3CO_2H \times 1.5$ $H_2O$ (MW=978.90): MS: $[M+H]^+=491$. Anal: Calculated: %C 40.49; %H 4.74; %N 7.15; %F 23.28; %H$_2$O 2.76. Found: %C 40.11; %H 4.77; %N 6.68; %F 23.51; %H$_2$O 2.77.

Step 5

Preparation of Boc-Leu-Lys-N$^\epsilon$(i-Pr, Z)-Pro D-Ala Amide (a.a. 7–10 of SEQ. ID. NO. 2)

In a clean, dry 5 L vessel charge 1.9 L EtOAc followed by 580.0 g (0.558 mol) TFA-lysine-N(i-Pr, Z)-proline-D-alanine amide (stoichiometry based on the starting 9/10 TFA salt). Stir to effect solution then cool to 0–5° C. and add sequentially 0.5 L (4.500 mol) N-methyl morpholine, 39.0 g (0.558 mol) Boc-leucine hydrate, 75.4 g (0.558 mol) HOBt, and 115.2 g (0.558 mol) DCC. The reaction mixture is warmed to 20–25° C., stirred for 15 hrs then cooled to 0° C. and filtered. The collected solids are washed with 100 mL EtOAc. The combined EtOAc filtrate is washed successively with 2×1 L 10% aq. citric acid, 2×1 L sat. aq. sodium bicarbonate and then with 2×1 L brine. The EtOAc layer is dried over MgSO$_4$, filtered and concentrated to yield 340.0 g of the protected tetrapeptide in 87% over-all yield from the 9/10 dipeptide TFA salt. For $C_{36}H_{58}N_6O_8 \times 0.5$ $H_2O$ (MW=711.91): MS: $[M+H]^+=703.6$. Anal: Calculated: %C 60.73; %H 8.35; %N; 11.81; %H$_2$O 1.27. Found: %C 60.66; %H 8.31; %N 11.33; %H$_2$O 1.34.

Step 6

Preparation of TFA-Leu-Lys-N$^\epsilon$(i-Pr, Z)-Pro-D-Ala Amide

In a clean, dry 5 L 3 necked round bottom flask (RBF), charge 3.5 Kg TFA. Cool to 0° C. and charge 340.0 g (0.558 mol) crude Boc-leucine-lysine-N*(i-Pr, Z)proline D-alanine amide with stirring. Stir the reaction at 0–5° C. for 2.0 hrs then concentrate to dryness under vacuum. Azeotropically remove residual TFA by adding 1.0 L toluene, and concentrating to dryness. Dry the product further under vacuum (12–15 Torr) to yield 577.0 g of crude product as an oil in quantitative yield. Dilute the crude oil with 1.6 L MTBE and heat to 50–55° C. Cool the slurry to 25° C. and slowly add 3.2 L hexane with stirring to precipitate the product. Cool the solution to 5° C. and stir for 0.5 hour. Isolate the product by vacuum filtration. Wash the white filter cake solid with 0.5 L 2:1 hexane: MTBE. Dry the wet cake under vacuum (150 Torr @ 25° C.) to afford 346.0 g of the tetrapeptide TFA salt as a white powder in 86.5% over-all yield from the 9/10 dipeptide TFA salt.

For recrystallization charge 342.0 g of the crude tetrapeptide TFA salt to a 2 L round bottom flask and add 1.0 L of MeCN. With agitation, heat the slurry to 50–55° C. to effect solution and continue heating to 65° C. whereupon the solution is filtered through celite. The celite pad is washed with 100 mL of MeCN and the combined filtrate/washes are cooled to 50 and stirred for 2 hrs followed by by vacuum filtration. The damp cake is washed with 100 mL of cold (5° C.) MeCN and the solid dried under vacuum (150 Torr @ 30° C.) for 12 hrs. to recover 175.0 g of the pure tetrapeptide salt. For $C_3H_{50}N_6O_6 \times 1.1 CF_3CO_2H \times H_2O$ (MW=746.21): MS: $[M+H]^+=603.4$. Anal: Calculated: %C 53.44; %H 7.17; %N 11.32; %F 8.40; %H$_2$O 2.96. Found: %C 53.40; %H 7.11; %N 11.32; %F 8.26; %H$_2$O 2.41.

EXAMPLE 2

Synthesis of 5/6 Fragment of Azaline B

Boc Aph(Atz)-D-Aph(Atz)OH

Step 7

Preparation of Boc-L-pNitroPhe-D-p-NitroPheOMe

To a 2000 ml 3-necked glass reaction flask equipped with a mechanical stirrer, addition funnel, thermocouple and nitrogen inlet was added 31.0 g (100.0 mmol) of Boc-L-p-nitroPhe-OH and 350 ml of THF. The solution is stirred in a dry ice/IPA bath at −15 degrees C. and 13.7 g (101.0 mmol) of IBCF is added in one portion, followed by the dropwise addition of 10.2 g (101.0 mmol) N-methyl morpholine in 25.0 ml of THF during 10–15 minutes. The temperature is maintained at −10 degrees C. for 1.25 hours. Then 26.0 g (100.0 mmol) of D-p-nitroPheOMe hydrochloride is added in one portion, followed by the dropwise addition of 10.2 g (100.1 mmol) N-methyl morpholine in 25.0 ml of THF during 10–15 minutes. The temperature is maintained at −10 degrees C. during the addition and the reaction slurry was stirred for 2 hours. The reaction mixture is allowed to warm to 5 degrees C. whereupon 400 ml of distilled water is added dropwise in 30 minutes followed by stirring for 1 hour as the reaction mixture warmed to room temperature. The slurry is filtered and the wet filter cake is washed with 2×200 ml portions of distilled water. The solid is air dried overnight then dried in a vacuum oven 24 hours at 40 degrees C. to yield: 48 g ( 93 % ) of the Boc dipeptide with m.p. 189–191 deg C. For $C_{24}H_{28}N_4O_9$ (MW=516.31): MS: $[M+H]^+=517$; $[M+Na]^+=539$. Anal: Calculated: %C 55.81; %H 5.46; %N 10.85. Found: %C 55.90; %H 5.42; %N 10.76.

Step 8

Preparation of Boc-p-Aph-D-p-AphOMe

To a 2000 ml Parr bottle is added 184.0 g (356.0 mmol) of the bis-nitro ester from Step 7and 1000 ml isopropanol and 300 ml ethyl acetate plus 14.0 g 5% Pd/C catalyst (50% wet) in one portion under an atmosphere of argon gas. The slurry is shaken under 50 psi of hydrogen for 6 hours. The hydrogenation is mildly exothermic with the temperature rising to 50–55 degrees C. The catalyst is removed by vacuum filtration thorough Celite and the catalyst residue is washed once with 50 ml ethyl acetate. The nearly colorless clear solution is evaporated in vacuo at 45 degrees C. and 900 ml of solvent is removed. The remaining solution is diluted with 800 ml hexane to yield a white crystalline solid. An additional 400 ml of hexane is added to improve stirring. The solid is collected by vacuum filtration in a 650 ml fritted glass funnel and the filter cake is washed once with 200 ml hexane. The white solid is air dried 4 hours, followed by drying in vacuum oven at 45 degrees C. for 24 hours to yield 155.4 g (95%) of Boc-p-Aph-D-Aph oMe; m.p.: 117–119 deg C. For $C_{24}H_{32}N_4O$ (MW=456.55): MS: $[M+H]^+=457$; $[M+Na]^+=479$. Anal: Calculated: %C 63.14; %H 7.07; %N 12.27. Found: %C 63.18; %H 6.92; %N 12.23.

Step 9

Preparation of Boc-p-Aph(Atz)-p-D-Aph(Atz)OMe

To a 3000ml 3-necked glass reaction flask equipped with a mechanical stirrer, addition funnel, thermocouple and nitrogen inlet is added 154.0 g (337 mmol) of Boc-p-Aph-D-p-AphOMe, 215.1g (903mmol) diphenylcyanocarbonimidate and 1625 ml of DMF. The solution is stirred for 16 hours at ambient temperature then cooled to −5 degrees C. whereupon a solution of 44.8 g (896 mmol) hydrazine monohydrate in 600 ml of DMF is added dropwise in 0.5 hours, maintaining the temperature below 5 degrees C. The solution is stirred and allowed to warm gradually to room temperature over a 3 hour period during which time a white solid begins precipitating. The mixture is stirred overnight at room temperature and the solid collected by vacuum filtration. The filter cake is washed successively with with 600 ml of DMF, 2×400 ml portions of isopropanol and 2×300 ml portions of MTBE. The solid is air dried 4 hours, followed by drying in a vacuum oven at 55 degrees C. for 16 hours to yield: 197.3 g (94%) of the fully elaborated dipeptide ester with m.p. 217–220 deg C. For $C_{28}H_{36}N_{12}O_5 \times 1.25 H_2O$ (MW=643.19): $[M+H]^+=621$; $[M+Na]^+=643$. Anal: Calculated: %C 52.29; %H 6.03; %N 26.13. Found: %C 52.57; %H 5.81; %N 25.78.

Step 10

Preparation of Boc-p-Aph(Atz)-p-D-Aph(Atz)OH

To a 2000 mL 3-necked glass reaction flask equipped with a mechanical stirrer and addition funnel is added 130 g (209.0 mmol) of Boc-p-Aph(Atz)-p-D-Aph(Atz)OMe, 500 mL of distilled water and 500 mL of methanol. The resultant slurry is stirred at room temperature and 575 mL of 1 N sodium hydroxide (575.0 mmol) is added dropwise over 10–20 minutes. The reaction mixture is stirred for an additional 2.5 hours and vacuum filtered through a Celite pad. The filtrate is stirred vigorously and acidified to pH 4.5 by slow, dropwise addition of 340 mL of 50% acetic acid-distilled water (v/v). The resultant granular slurry is filtered and the wet filter cake is washed with 600 mL of distilled water and air dried for about an hour. The nearly dry filter cake is transferred to a vacuum oven and dried overnight at 40° C. to afford: 111.5 g (88%) of the Boc ⅚ dipeptide acid with mp: ca. 208 deg C. (dec). For $C_{27}H_{34}N_{12}O_5$ (MW=606.64): MS: $[M+H]^+=607$. Anal: Calculated: %C 53.46, %H 5.65; %N 27.71. Found: %C 53.36; %H 5.72; %N 27.41.

EXAMPLE 3

Synthesis of ¼ fragment of Azaline B

Ac-β-D-2NAL-(4Cl)D-Phe-D-3PAL-SerOH (a.a. 1–4 of SEQ. ID. NO. 2)

Step 11

Preparation of Boc-D-NAL-D-CalOMe

A suspension of 5.0g (20 mmol) of H-D-p-Cal-OMe HCl and 6.3g (20 mmol) of Boc-D-Nal-OH in 80 ml of MeCN is stirred at room temperature in a 250 ml flask. Following the addition of 20 ml of DMF the suspension is stirred, cooled to<0° C. and treated sequentially with 2.7 g (20 mmol) of HOBt, 8.7 g (23 mmol) of HBTU and 12 ml (69 mmol) of DIPEA while maintaining the temperature 0° C. at all times. The resulting clear solution is stirred at 0° for 1 hr and then the reaction mixture is added to 180 ml of cold distilled water whereupon the product precipitates as a white solid. This is collected by filtration, washed with 50 ml of distilled water and then dried at 50–55° C. under vacuum (24–25") to yield: 9.77 g, 94% of the dipeptide ester. For $C_{28}H_{31}ClN_2O_5$ (MW=511.02) Anal: (Calculated): %C 65.81; %H 6.11; %N 5.48; %Cl 6.94. Found: %C 65.01; %H 6.31; %N 5.69; %Cl 6.82.

Step 12

Preparation of H-D-NAL-D-CalOMe.HCl

A suspension of 1100 g (2.15 mol) of Boc-D-Nal-D-p-Cal-OMe is stirred in 10.2 L of 3N HCl (g)/ MeOH in a 22 L reaction flask at 35–40° C. until dissolution occurs. The solution is allowed to stir and cool to room temperature. The reaction mixture is added to 33.0 L of cold distilled water maintaining the temperature at 20° C. The product precipitates as a thick white solid which is collected by filtration and washed with 2.0 L of distilled water and then dried at 35–40° C. under vacuum (24–25") to yield: 885 g, 90.0% of the dipeptide salt. For $C_{23}H_{23}ClN_2O_3 \times HCl$ (MW=447.36): Anal: (Calculated): %C 61.75; %H 5.41; %N 6.26; %Cl 15.85. Found: %C 61.41; %H 5.50; %N 6.21; %Cl 15.66.

Step 13

Preparation of Ac-D-2-NAL-D-p-Cal-OMe

In a 1.0 liter reaction flask equipped with a stirrer, thermometer, nitrogen inlet, condenser and cooling bath, at room temperature, is added 516 ml of DMF followed by 70.0 g (0.156 mol) of H-D-2-NAL-D-p-Cal-Ome×HCl. The resulting mixture is cooled to <−5° C. To this cold solution is added 49.02 g (0.484 mol) of TEA followed by the slow addition of 17.55 g (0.171 mol) of acetic anhydride. Additions are maintained at (−1° C.) and the reaction suspension is allowed to stir at −1° C. to −5° C. for approximately 1 hr. The reaction suspension is acidified at -5–0° C. by the slow addition of a solution of 34.4 ml HOAc/860 ml water. The slurry is then stirred for 1 h at −5–0° C. and the product isolated by vacuum filtration, washed with 1000 ml of cold water and air dried. The wet cake is added to a 1.0 liter flask containing 420 ml of methanol. The mixture is heated with stirring to 35° C., cooled to room temperature and the product isolated by vacuum filtration to give 80.1 g of a wet solid. The solids are dried to a constant weight at 30–35° C. under vacuum to yield 60.57 g (85.7%.) of the acetylated dipeptide ester. For $C_{25}H_{25}ClN_2O_4$ (MW=452.94): MS: $[M+H]^+=453$. Anal: (Calculated): %C 66.30; %H 5.56; %N 6.18; %Cl 7.82. Found: %C 66.11; %H 5.66; %N 6.21; %Cl 7.77.

Step 14

Preparation of Ac-D-NAL-D-CalOH

A suspension of 800 g (1.77 mol) of Ac-D-2-Nal-D-p-Cal-OMe in 8.0 L of THF in a 22 L reaction flask is stirred at −12° C. Add 1.28 kg (1.97 mol) of 40% aqueous n-Bu$_4$NOH slowly while maintaining the temperature at <−3° C. at all times. After 30 min the reaction is acidified at −8° C. by a slow addition of 710 ml of 6M HCl. The resulting clear solution is diluted with 1.78 L of distilled water and most of the THF is distilled off at 25–30° C. and 23–25" Hg producing a thick slurry which is diluted with methanol and the solid collected by filtration. The flask and the solid are rinsed with 2.0 L of methanol and then dried at 35–40° C. under vacuum (24–25") to yield: 697.1 g (88%) of the acetylated dipeptide acid. For $C_{24}H_{23}ClN_2O_4$ (MW=438.91): MS: $[M+H]^{30}=439$. Anal. (Calculated): %C 65.68; %H 5.28; %N 6.38; %Cl 8.08. (Found): %C 65.23; %H 5.38; %N 6.24; %Cl 8.20.

Step 15

Preparation of Boc-D-3-PAL-Ser-OBn

To a 2.0 liter reaction flask under N$_2$ is added 1.1 liters of DMF. With stirring at rt, 129.72 g (0.487 mol) of Boc-D-3-Pal-OH is added followed by 116.0 g (0.500 mol) of H-L-Ser-OBn HCl. After stirring for 0.25 hr the resulting solution is cooled to 0° C.-(−1° C.) and 9.20 g of HOBt is added followed by 115.0 g of NMM (1.14 mol) during approximately 20 min while maintaining the temperature at −1 to 0° C. To this solution is then added 98.9 g of WSDCl (0.505 mol). After stirring overnight at 0°, the reaction mixture is filtered and the clear filtrate is added to a stirred mixture of 2760 ml ice/water in a 12.0 liter flask. The resulting thick suspension is diluted with an additional 500 ml of cold water and stirred for 1.0 hr. The product is collected by vacuum filtration and washed with 5×1000 ml of water. The wet product ( 504 g ) is dried under vacuum at 35–45° C. to a constant weight. The material is then powdered in a mortar and pestle to afford 196.0 g of the dipeptide salt as a homogeneous white solid in 90.8% yield. For $C_{23}H_{29}N_3O_6\times0.5\ H_2O$ (MW=452.61): MS: [M+H]$^+$= 444. Anal: Calculated: %C 61.04; %H 6.68; %N 9.28; %H$_2$O 1.99. Found: %C 61.25; %H 6.66; %N 9.28; %H$_2$O 1.71.

Step 16

Preparation of H-D-PAL-Ser(OH)-OBn 2 HCl

To a 2.0 liter reaction flask is added 1.562 liters of 1,2-dichloroethane followed by 189.0 g of Boc-D-3-Pal-Ser-OBn (0.42 mol). The mixture is stirred and heated to 40–45° C. to effect solution which is then added under N$_2$ during approximately 0.5 hrs to a 5.0 liter flask containing 2.0 L of cold (0–5°)3N HCl/EtOAc. The resulting suspension is stirred for approx. 1.0 hr after which the product is isolated by vacuum or pressure filtration and washed with 2×1.0 liters of fresh EtOAc under a nitrogen atmosphere. The product is removed from the filter under a nitrogen atmosphere as quickly as possible and dried under vacuum at 30–35° C. to a constant weight to yield 172.7 g (97.5%) of the hygroscopic dipeptide hydrochloride salt. For $C_{18}H_{21}N_3O_4\times2HCl\times0.8\ H_2O$(MW=430.72): MS: [M+H]$^+$= 344. Anal: Calculated: %C 51.93; %H 5.57; %N 10.09; %Cl 17.03; %H$_2$O 3.35. Found: %C 50.18; %H 5.73; %N 9.64; %Cl 15.92; %H$_2$O 3.52.

Step 17

Preparation of Ac-D-NAL-D-pCal-D-3-PAL-Ser-OBn (SEQ. ID. NO. 5)

A mixture of 175.38 g (0.4 mol) of Ac-D-NAL-D-Cal-OH and 166.72 g (0.4 mol) H-D-PAL-Ser-OBn 2 HCl is dissolved in 2.60 L of DMF in a 5 L reaction flask at room temperature and then cooled to 0° C. The clear solution formed a hard gel on cooling to which is added 0.6 L of DMF to produce a stirrable mixture. To this is added 55.5 g (0.41 mol) of HOBt and 218.1 g of DIPEA (1.65 mol) at −2 to 0° C. and the mixture stirred until the gel dissolved. The clear solution is then treated with 160 g of HBTU (0.42 mol) and stirred for 1 hr at −2 to 0° C. after which the reaction mixture is added to a mixture of 3.30 L of MeOH and 0.88 L distilled water. An additional 1.10 L of MeOH is used to rinse the flask and combined with the previous mixture. The product is precipitated slowly by stirring the aqueous MeOH mixture at room temperature. After 1 hr the resulting solid is collected by filtration and washed with 1.0 L of MeOH and dried at 30–35° C. under vacuum (24–25") to yield 293.3 g (92.6%) of the tetrapeptide. For $C_{42}H_{42}ClN_5O_7$ (MW=764.15): MS: [M+H]$^+$=764. Anal: Calculated: %C 66.03; %H 5.54; %N 9.16; %Cl 4.64. Found: %C 65.49; %H 5.57; %N 9.12; %Cl 4.74.

Step 18

Preparation of Ac-D-2-Nal-D-p-Cal-D-3-Pal-Ser-OH (SEQ. ID. NO. 5)

After powdering 261.45 g (0.342 mol ) of Ac-D-NAL-D-p-Cal-D-3-PAL-Ser-OBn (SEQ. ID. NO. 5) to a fine solid, it is suspended in 1.80 liters of THF then stirred and cooled to −5° C. The cold suspension is treated with 443.7 g ( 0.684 mol ) of 40% aqueous n-Bu$_4$NOH, added at such a rate that the reaction temperature did not exceed −2° C. (about 30 min). The solid dissolved slowly after the base is added to afford a slightly turbid solution. After 3.5 hr the turbid reaction mixture is filtered and the clear filtrate added slowly, with good stirring, into 4.95 liters of ice/water containing 57 ml (0.684 mol ) of 12M HCl. After stirring for 0.5 hr at pH =4.2, the thick white precipitate is collected by filtration and the damp cake is washed with 4×1.0 L of water, air dried under vacuum briefly and then slurried in 9.50 L of hot water (65° C.) for 1 hr and filtered. The wet cake is air dried under vacuum briefly, slurried in 3.825 liters of MeOH and stirred under reflux. The suspension is filtered hot (600) and the damp cake is washed with 1.0 liter of MeOH then dried under vacuum at 35–40° to a constant weight to afford 174.6 g (75.7%) of the acetylated tetrapeptide acid. For $C_{35}H_{36}ClN_5O_7\times0.66\ H_2O$ (MW=686.05): MS: [M+H]$^+$= 674. Anal: Calculated: %C 62.36; %H 5.38; %N 10.39; %Cl 5.26; %H$_2$O 1.73. Found: %C 61.01; %H 5.46; %N 10.04; %Cl 5.16; %H$_2$O 1.72.

EXAMPLE 4

Coupling of 5/6 and 7/10 Fragments

Boc Aph(Atz)-D-Aph(Atz)-Leu-Lys(ε-Z, ε-iPr)-Pro-D-Ala-NH$_2$ (a.a. 5–10 of SEQ. ID. NO. 2)

STEP 19

Preparation of Boc-Aph(Atz)-D-Aph(Atz)-Leu-Lys (ε-Z, ε-iPr)-Pro-D-Ala-NH$_2$ (a.a. 5–10 of SEQ. ID. NO. 2)

To a 2000 ml 3-necked glass reaction flask equipped with a mechanical stirrer, addition funnel, thermocouple and nitrogen inlet is added 16 g (91.4 mmol) of H-Leu-Lys-N (ε-Z, ε-iPr)-Pro-D-Ala-NH$_2$×TFA (a. a. 7–10 of SEQ. ID. NO. 2) and 530 ml DMF. The solution is stirred at room temperature and 14.68 g (95.9 mmol) of HOBt is added in one portion followed by 59.72 g (80.4 ml) (462.1 mmol) of DIPEA in one portion. An additional 350 ml DMF was added followed by 54.59 g (90.0 mmol) of Boc-p-Aph(Atz)-p-D-Aph(Atz)OH in one portion. After stirring for 1 hour the clear reaction solution is cooled to 0° C. in an IPA/dry ice bath and 31.78 g (99.0 mmol) of TBTU is added in one portion. The reaction solution was stirred at 0–5° C. for 2 hrs after which time the excess DIPEA and 440 ml of DMF is removed by evaporation in vacuo at <40 degrees C. The solution (total vol - 700 ml) is warmed to 35° C. and added dropwise in 0.5 hr to a rapidly stirred cold (10°) solution of 3520 ml of 5% acetic acid containing 176 g (2.28 mol) of ammonium acetate. The creme colored suspension was stirred for 1 hr and the precipitate is collected by vacuum filtration. The filter cake is washed successively with 2×250 ml portions of distilled water, 2×250 ml portions of 5% sodium carbonate solution and 2×250 ml portions of distilled water. The creme colored solid is air dried 16 hours, followed by drying in vacuum oven at 50 degrees C. for 24 hrs to yield 95.9 g (89%) of the Boc hexapeptide fragment. For $C_{58}H_{82}N_{18}O_{10}\times2.25\ H_2O$ (MW=1231.95): [M+H]$^+$= 1191.3; [M+Na]$^+$=1213.5. Anal: Calculated: %C 56.55; %H 7.08; %N 20.47; %H$_2$O 3.29. Found: %C 56.87; %H 6.93; %N 19.90; %H$_2$O 3.54.

Step 20

Preparation of Aph(Atz)-D-Aph(Atz)-Leu-Lys(ε-Z, ε-iPr)-Pro-D-AlaNH$_2$×3TFA×2H$_2$O (a. a. 5–10 of SEQ. ID. NO. 2)

To a 2000 ml 3-necked glass reaction flask equipped with a mechanical stirrer, thermocouple and nitrogen inlet is added 1211 g (818 ml, 10.62 mol) of TFA This is stirred and cooled to 0° C. whereupon 182 g (152.7 mmol) of Boc-Aph (Atz)-D-Aph(Atz)-Leu-Lys(ε-Z-iPr)-Pro-D-AlaNH$_2$ is added in four equal portions every 15 minutes. The light brown reaction solution was stirred for 2 hr at 0–5° C. The TFA was removed by evaporation in vacuo at <40° C. to afford an oily residue from which the product is precipitated by addition of 2400 ml of MTBE with rapid stirring to produce a creme colored solid. The solid is isolated by vacuum filtration and the filter cake is washed once with 800 ml of MTBE. The solid is air dried 3 hours, followed by drying in vacuum oven at 50° C. for 24 hours to yield 220.5g (98%) of the hexapeptide salt. For $C_{53}H_{74}N_{18}O_8$×3 $CF_3CO_2H$×2 H$_2$O (MW=1469.39): MS: [M+H]$^+$=1091. Anal: Calculated: %C 48.23; %H 5.56; %N 17.17; %F 11.63, %H$_2$O 2.45. Found: %C 48.16; %H 5.54; %N 17.37; %F 11.50, %H$_2$O 3.26.

EXAMPLE 5

Coupling of 5/10 and 1/4 Fragments

Ac-β-D-2NAL-p-D-Cal-D-3PAL-Ser-Aph(Atz)-D-Aph(Atz)-Leu-Lys(ε-Z, ε-iPr)-Pro-D-Ala-NH$_2$
(SEQ. ID. NO. 6)

Step 21

Preparation of Ac-D-NAL-D-Cal-D-PAL-Ser-Aph (Atz)-D-p-Aph(Atz)-Leu-Lys(ε-Z, ε-iPr)-Pro-D-AlaNH$_2$ (SEQ. ID. NO. 6)

To a 1000 ml 3-necked glass reaction flask equipped with a mechanical stirrer, thermocouple and nitrogen inlet is added 78.27 g (53.2 mmol) of Aph(Atz)-D-Aph(Atz)-Leu-Lys(ε-Z, ε-iPr)-Pro-D-AlaNH$_2$×3TFA×2H$_2$O (a. a. 5–10 of SEQ. ID. NO. 6)and 390 ml DMF. The solution is stirred at room temperature and 8.08 g (49.5 mmol) of HOOBt was added in one portion followed by 40.5 g (54.6 ml) (313.3 mmol) of DIPEA in one portion. Then 31.85 g (47.3 mmol) of Ac-D-2-NAL-D-p-Cal-D-3-PAL-Ser-OH (SEQ. ID. NO. 5) is added in one portion. After stirring for 1 hour the clear, yellow reaction mixture was cooled to 0° C. in an IPA/dry ice bath and 16.69 g (52.0 mmol) of TBTU was added in one portion. The reaction solution is stirred at 0–5° C. two hrs after which time the excess DIPEA and 195 ml of DMF is removed by evaporation in vacuo at <40° C. The amber colored solution (total vol 250 ml) was warmed to 35° C. and added dropwise during 0.5 hrs to a rapidly stirred, cold (10°) solution of 1560 ml of 5% acetic acid containing 156 g (2.02 mol) of ammonium acetate. The pale yellow suspension is stirred for 1 hr and the precipitate is collected by vacuum filtration. The filter cake is washed successively with 2×250 ml portions of distilled water, 2×250 ml portions of 5% sodium carbonate solution and 2×250 ml portions of distilled water. The pale yellow solid is air dried 16 hours then dried in a vacuum oven at 50° C. for 24 hrs to yield: 80.1 g (96%) of the protected decapeptide. This is purified by preparative HPLC on a Kromasil KR 100-C8 packed column maintained @ 30–38° and monitored @ 240 nm. Isocratic elution with A: 36% MeCN/H$_2$O+20 mmol TEAP at pH=2.5–2.7 and B: 60% MeCN/H$_2$O @ 484 ml/min affords the protected decapeptide of at least 95% purity after precipitation with NH$_4$OH. For $C_{88}ClH_{23}O_{14}$×3.5 H$_2$O (MW=1810.79): MS: [M+H]$^+$=1747.4; [M+2H]$^+$=874.0. Anal: Calculated: %C 58.37; %H 6.40; %N 17.79; %Cl 1.96; %H$_2$O 3.48. Found: %C 58.58; %H 6.28; %N 17.37; %Cl 2.09; %H$_2$O 3.38.

EXAMPLE 7

Deprotection

Ac-β-D-2NAL-p-D-Cal-D-3PAL-Ser-Aph(Atz)-D-Aph(Atz)-Leu-Lys(ε-iPr)-Pro-D-Ala-NH$_2$ (SEQ. ID. NO. 6)

Step 22

A mixture of 27.0 g (15.47 mmol) Ac-D-NAL-D-Cal-D-PAL-Ser-Aph(Atz)-D-p-Aph(Atz)-Leu-Lys(ε-Z, ε-iPr)-Pro-D-AlaNH$_2$ (SEQ. ID. NO. 6) (1613.3 g/mol), 27.0 g (249.68 mmol) of anisole and 14.0 g (187.79 mmol) potassium chloride (KCl) in 300 mL trifluoroacetic acid is heated in a water bath at 50–55° C. and stirred for 1–1.5 h. After all of the starting material had been consumed the heating bath is removed and the resulting warm, clear TFA solution is added with stirring to a 2L separatory funnel containing 1.1 L of icetwater. The product precipitates as a white solid. The solid is extracted into 400 mL of ethyl acetate and the reaction flask is rinsed with 150 mL of ethyl acetate. The combined organic extracts are washed with 400 mL of 5% aqueous NaCl solution. The EtOAc layer is separated and basified by addition of 300 mL of saturated ammonium hydroxide solution whereupon Azaline B free base precipitates as a white solid. The biphasic mixture is filtered to collect the product which is air-dried briefly, slurried in 300 mL of ethyl acetate and filtered to remove any organic impurities. After drying, the free base is reslurried in 400 mL of distilled water containing 15 mL of saturated ammonium hydroxide to remove most of the residual TFA. The solid is collected by filtration, washed with water and air dried to yield 21.5 g, (86.2%) of Azaline B free base. The crude free base is purified on a Kromasil C-18 packed column maintained at 250 and monitored at 300 nm. The column is preequilibrated with 15% MeCN/H$_2$O containing 0.2% TFA. After increasing the MeCN concentration to 20% the product (as the trifluoroacetate salt) was eluted using a linear gradient of 20–30% MeCN. Azaline B free base was precipitated from pooled HPLC fractions upon addition of NH$_4$OH. For Azaline B free base $C_{80}H_{102}ClN_{23}O_{12}$ (MW=1613.30): MS: [M+H]$^+$=1613.

Step 23

Preparation of Azaline B Acetate

Azaline B free base (Ac-p-D-2NAL-p-D-Cal-D-3PAL-Ser-Aph(Atz)-D-Aph(Atz)-Leu-Lys(ε-iPr)-Pro-D-Ala-NH$_2$), (SEQ. ID. NO. 6) 69.1 g (42.87 mmol) is dissolved in 300.0 mL of glacial acetic acid by heating on a steam bath to about 100° C. The resulting solution is filtered to remove any insolubles or dust using a total of 50 mL of glacial AcOH for the rinse. The AcOH solution was then diluted with 2 L of ethyl acetate and 100 mL of methanol to precipitate AzB acetate. The salt is collected by filtration, washed with 500 mL of EtOAc and air dried. For $C_{80}H_{102}ClN_{23}O_{12}$×1.25 $CH_3CO_2H$×4.5 H$_2$O (MW=1769.44). Anal: Calculated: %C 56.00; %H 6.61; %N 18.21;

%Cl 2.00; %H₂O 4.58; %HOAc 4.24. Found: %C 56.30; %H 6.58; %N 17.85; %Cl 1.98; %H₂O 4.50; %HOAc 4.48; %TFA 0.2. For MS/MS B ions: Calculated: 240.1, 421.1, 569.2, 656.2, 900.3, 1144.4, 1257.5, 1427.7, 1524.7, 1595.7. Observed: 240.1, 421.1, 569.2, 656.2, 900.3, 1144.4, 1257.5, 1427.7. For MS/MS Y ions: Calculated: 1570.8, 1373.7, 1192.7, 1044.6, 957.6, 713.5, 469.4, 356.3, 186.1, 89.1. Observed: 1192.7, 1044.6, 957.6, 713.5, 469.4, 356.3.

---

We claim:

1. A liquid phase synthetic method for preparing a GnRH peptide analog of Formula 1:

G-$AA_1$-(A)D-Phe-$AA_3$-$AA_4$-($R_2$)$AA_5$–$AA_6$-$AA_7$–$AA_8$-Pro-$AA_{10}$-$NH_2$ (SEQ. ID. NO. 3)

Formula 1 or an acid addition salt thereof, wherein G is an acyl group having 7 or less carbon atoms; $AA_1$ is (A)D-Phe, (B)D-Trp, or β-D-NAL; A is H, Cl, F, $NO_2$, Br, $CH_3$, or $OCH_3$; B is H, NO2, NH2, $OCH_3$, F, Cl, Br or $CH_3$; $AA_3$ is D-PAL, β-D-NAL or (B)D-Trp; $AA_4$ is Ser or $P_1$-Ser wherein $P_1$ is a hydroxy protecting group; $R_2$ is H, $NaCH_3$ or $NaCH_2CH_3$; $AA_5$ is Aph($P_2$), Aph(Ac), Aph(atz), Lys($P_2$), Lys(atz), Aph (Q-Atz) or Lys(Q-Atz); $AA_6$ is D-Aph($P_2$), D-Aph(ac), D-Aph(atz), D-Lys($P_2$ ), D-Lys(atz), D-Aph(Q-Atz) or D-Lys(Q-Atz); wherein $P_2$ is an amino protecting group; Ac is acetyl, atz is 5'-(3'-amino-1H-1',2',4'-triazolyl), and Q is an amino acid residue; selected from P-Ala, Gly, GABA, the D- and L- isomers of Ala, amino isobutyric acid, 6-aminohexanoic acid, Ser, Thr, His, Tyr, Asn, and Gln$AA_7$ is Leu, NML, Nle or Phe; $AA_8$ is iPr-Lys, ($P_2$)iPr-Lys, or Arg; $AA_{10}$ is D-Ala, Gly, $NH_2NHCO$ or $NH(R_3)$ wherein $R_3$ is lower alkyl; is provided, which comprises:

(a) reacting a peptide of the formula:

T-($R_2$)$AA_5$–$AA_6$-X where T is (P2) $AA_4$ or $P_2$ and X is $AA_7$—OH or is —OH, with a peptide of the formula:

X'- $AA_8$-Pro-$AA_{10}$-$NH_2$ or acid-addition salt form thereof, where X' is $AA_7$ when X is absent and X' is absent when X is $AA_7$—OH;

in a liquid reaction medium in the presence of a peptide coupling reagent and a strong organic amine base to obtain a product of the formula:

T-($R_2$)AAS-$AA_6$-$AA_7$–$AA_8$-Pro-$AA_{10}$-$NH_2$;

(b) removing the $P_2$ protecting group at the N-terminus, and (c) reacting the product of step (b) or an acid addition salt thereof, with a peptide of the formula:

G-$AA_1$-($R_1$)D-Phe-$AA_3$-T' or acid-addition salt form thereof, where T' is AA$_4$—OH when T is absent and is absent when T is P$_2$-AA$_4$, in a liquid reaction medium to obtain a GnRH peptide of the formula:

G-AA$_1$-(A)D-Phe-AA$_3$-AA$_4$-(R$_2$)AA$_5$-AA$_6$-AA$_7$-AA$_8$-Pro-AA$_{10}$-NH$_2$. (SEQ. ID. NO. 3)

2. The process of claim 1 wherein the GnRH peptide of Formula 1 is selected from the peptides wherein G is an acyl group having 7 or less carbon atoms; AA$_1$ is β-D-NAL; A is 4Cl; AA$_3$ is D-PAL;; AA$_4$ is Ser, R$_2$ is H, N$^\alpha$CH$_3$ or N$^\alpha$CH$_2$CH$_3$ ;AA$_5$ is Aph(Ac),Aph(atz), Lys(atz), Aph(Q-Atz) or Lys(Q-Atz); AA$_6$ is D-Aph(ac), D-Aph(atz), D-Lys (atz), D-Aph(Q-Atz) or D-Lys(Q-Atz); wherein ac is acetyl, atz is 5'-(3'-amino-1H-1',2',4'-triazolyl), and Q is the acyl residue of an amino acid selected from β-Ala, Gly, GABA, the D- and L-isomers of Ala, amino isobutyric acid, 6-amino-hexanoic acid, , Ser, Thr, His, Tyr, Asn and Gln; AA$_7$ is Leu; AA$_8$ is ipr-Lys; and AA$_{10}$ is D-Ala.

3. The process of claim 1 wherein the GnRH peptide of Formula I is Azaline B; Ac-β-D-2NAL-(4Cl)D-Phe-D-3PAL-Ser-Aph(Atz)-D-Aph(Atz)-Leu-Lys(isopropyl)-Pro-D-Ala-NH$_2$ (SEQ ID No:2), or its acid addition salt.

4. The process of claim 1 comprising the steps of reacting:
(a) a peptide of the formula:

T-(R$_2$)AA$_5$-AA$_6$—OH where T is Boc, with a peptide of the formula:

X'-AA$_8$-Pro-AA$_{10}$-NH$_2$ or acid addition salt thereof, where X' is AA$_7$;
in a liquid reaction medium medium in the presence of a peptide coupling reagent and a strong organic amine base to obtain a product of the formula:

T-(R$_2$)AA$_5$-AA$_6$-AA$_7$-AA$_8$-Pro-AA$_{10}$-NH$_2$ (b) removing the Boc protecting group at the N-terminus by treatment with a suitable acid, and
(c) reacting the product of step (b) or an acid addition salt thereof with a peptide of the formula:

G-AA$_1$-(R$_1$)D-Phe-AA$_3$-AA$_4$—OH in a liquid reaction medium to obtain a GnRH peptide of the formula:

G-AA$_1$-(A)D-Phe-AA$_3$-AA$_4$-(R$_2$)AA$_5$-AA$_6$-AA$_7$-AA$_8$-Pro-AA$_{10}$-NH$_2$. (SEQ. ID. NO. 2)

5. The process of claim 1 wherein the peptide coupling reagent of step (a) is selected from DCC, DIC, TBTU, WSCDI, EEDQ, HBTU, TNTU, TSTU, HATU, BOP, BOP-Cl, PyBOP, PyBroP, IPCF, IBCF and propane phosphonic acid anhydride.

6. The process of claim 1 wherein the strong organic amine base of step (a) is selected from TEA or DIPEA.

7. The process of claim 6 wherein the strong organic amine base is DIPEA.

8. The process of claim 1 wherein the peptide coupling reagent of step (a) is TBTU with HOBT and the strong organic amine base is DIPEA.

9. The process of claim 1 wherein the solvent for the reaction of step (a) is selected from EtOAc, DCM, DMF, DMA, THF, NMP, DMSO, TFE, MTBE and MeCN.

10. The process of claim 9 wherein the solvent is DMF.

11. The process of claim 1 wherein the ε-amino group group on AA$_8$ is protected with a suitable amino protecting group selected from acetyl (Ac), benzoyl (Bz), trifluoroacetyl (Tfa), toluenesulfonyl (Tos), benzyl (Bn), triphenylmethyl (Trt), o-nitrophenyl-sulfenyl (Nps), benzyloxycarbonyl (Cbz or Z), t-butoxycarbonyl (Boc), allyloxycarbonyl (alloc), 9-fluorenylmethyloxycarbonyl (Fmoc), 2-bromo-benzyloxycarbonyl (2-Br-Z), 2-chloro-benzyloxycarbonyl (2-Cl-Z), t-butyl-dimethylsilyloxycarbonyl, [2-(3,5-dimethoxyphenyl)-propyl-2-oxycarbonyl] (Ddz), 2,2,2-trichloroethyloxycarbonyl (Troc), biphenylylisopropyloxycarbonyl (Bpoc), and o-nitrobenzyloxycarbonyl.

12. The process of claim 11 wherein the protecting group is benzyloxycarbonyl.

13. A liquid phase process for preparing a peptide of the formula:

wherein R$_1$ is P$_2$-Ser, P$_2$-Ser(P$_1$)- or P$_2$ where P$_1$ is a hydroxy protecting group and P$_2$ is an amino protecting group and R$_2$ is Leu, LeuOR where R is lower alkyl, OH or lower alkyl, is provided, which comprises:

a) reacting a compound of the formula P$_2$ -p-NO$_2$-PheOH with p-NO$_2$-PheOR where R is alkoxy, or an acid addition salt thereof, in the presence of a suitable peptide coupling reagent in a suitable solvent to obtain a dipeptide of the formula:

b) reducing the dipeptide to obtain a compound of the formula:

c) reacting the product of step b) first with diphenyl cyanocarbonimidate or an equivalent reagent and then with hydrazine in a suitable solvent to yield a compound of the formula:

14. In a process for the preparation of Azaline B acetate (Ac-β-D-2NAL-p-D-Cal-D-3PAL-Ser-Aph(Atz)-D-Aph(Atz)-Leu-Lys(ε-iPr)-Pro-D-Ala-NH$_2$), from the protected Azaline B precursor (Ac-D-NAL-D-Cal-D-PAL-Ser-Aph(Atz)-D-p-Aph(Atz)-Leu-Lys(ε-Z, ε-iPr)-Pro-D-AlaNH$_2$ (SEQ. ID. NO. 6), wherein first the protecting group is cleaved by treatment with a salt in the presence of trifluoroacetic acid and a cation scavenger at about −20 to 0° C. under an inert atmosphere and then the resulting product is purified by chromatography; the improvement comprising isolating the azaline B acetate by concentrating the combined fractions from the chromatographic purification by either:

(a) concentrating the Azaline B solution on a reverse phase HPLC flash column, and washing the concentrated material from the column with an organic solvent prior to ion-exchange; or (b) concentrating the solution after the ion-exchange using reverse osmosis;

and then recovering the purified Azaline B acetate by evaporation of the concentrated solution and precipitation of the Azaline B acetate from the acetic acid solution.

* * * * *